(12) United States Patent
Petersen et al.

(10) Patent No.: US 8,945,360 B2
(45) Date of Patent: Feb. 3, 2015

(54) HIGH-PERFORMING ELECTROPHORESIS GELS WITH EXTENDED SHELF LIVES

(75) Inventors: Shane Petersen, Fairfield, CA (US); Cory Panattoni, Winters, CA (US); Craig Rowell, Albany, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 160 days.

(21) Appl. No.: 12/691,440

(22) Filed: Jan. 21, 2010

(65) Prior Publication Data

US 2010/0187114 A1 Jul. 29, 2010

Related U.S. Application Data

(60) Provisional application No. 61/147,557, filed on Jan. 27, 2009.

(51) Int. Cl.
*C07K 1/26* (2006.01)
*G01N 27/447* (2006.01)

(52) U.S. Cl.
CPC ............ *C07K 1/26* (2013.01); *G01N 27/44747* (2013.01); *Y10S 436/826* (2013.01)
USPC ........... 204/469; 204/470; 204/450; 436/826; 252/62.2

(58) Field of Classification Search
CPC ... G01N 27/447; G01N 27/44747; C07K 1/26
USPC ................... 204/469, 470; 436/826; 252/62.2
See application file for complete search history.

(56) References Cited

U.S. PATENT DOCUMENTS

| | | | |
|---|---|---|---|
| 4,139,440 A | 2/1979 | Chrambach et al. | |
| 4,481,094 A | 11/1984 | Fernandez de Castro et al. | |
| 5,074,981 A | 12/1991 | Fairfield | |
| 5,464,516 A * | 11/1995 | Takeda et al. | 204/456 |
| 5,578,180 A * | 11/1996 | Engelhorn et al. | 204/468 |
| 5,589,393 A * | 12/1996 | Fiechtner et al. | 436/15 |
| 5,849,166 A * | 12/1998 | Fuller | 204/468 |
| 6,090,252 A * | 7/2000 | Bjellqvist | 204/468 |
| 6,726,821 B1 | 4/2004 | Suzuki | |
| 7,147,762 B2 * | 12/2006 | Bjellqvist et al. | 204/461 |
| 7,422,670 B2 * | 9/2008 | Updyke et al. | 204/456 |
| 2003/0221963 A1 * | 12/2003 | Bjellqvist et al. | 204/468 |
| 2005/0121325 A1 * | 6/2005 | Updyke et al. | 204/469 |
| 2006/0118418 A1 | 6/2006 | Sivaram et al. | |

FOREIGN PATENT DOCUMENTS

| | | | | |
|---|---|---|---|---|
| CN | 1327537 A | | 12/2001 | |
| DE | EP 0509388 | * | 9/1992 | ............ B01D 57/02 |
| EP | 0 566 784 A1 | | 10/1993 | |
| JP | 4-184163 A | | 7/1992 | |
| JP | 10-510363 A | | 10/1998 | |
| WO | 96/16724 A1 | | 6/1996 | |

OTHER PUBLICATIONS

Office Action from CN Appl. No. 201080006324.6, dated Mar. 17, 2014. (English translation).
Extended European Search Report mailed Mar. 11, 2013 for EP Patent Application No. 10736290.7, 6 pages.
International Search Report mailed Mar. 8, 2010 for PCT/US10/22056.

* cited by examiner

*Primary Examiner* — Luan Van
*Assistant Examiner* — Steven Rosenwald
(74) *Attorney, Agent, or Firm* — Kilpatrick Townsend & Stockton LLP

(57) ABSTRACT

Polyacrylamide gels that offer high resolution as electrophoretic media for protein separations and an improved resistance to hydrolysis upon storage are made by including either taurine, asparagine, or both as an ampholyte, in combination with either tris(hydroxymethyl)-aminomethane or bis(2-hydroxyethyl)amino-tris(hydroxymethyl)methane as a buffer, plus other conventional components.

32 Claims, No Drawings

HIGH-PERFORMING ELECTROPHORESIS GELS WITH EXTENDED SHELF LIVES

CROSS REFERENCE TO RELATED APPLICATION

This application claims the benefit of U.S. Provisional Patent Application No. 61/147,557, filed Jan. 27, 2009, the contents of which are incorporated herein by reference.

BACKGROUND OF THE INVENTION

1. Field of the Invention

This invention resides in the field of polyacrylamide electrophoresis and the polyacrylamide gels used in the electrophoresis.

2. Description of the Prior Art

The wide use of polyacrylamide gel electrophoresis (PAGE) in research and diagnostics, and in biochemistry laboratories in general, is due in large part to the optical transparency and electrical neutrality of polyacrylamide gels, and to the flexibility and adaptability of polyacrylamide gels to a wide range of molecular sizes of the species to be separated in the gel. This flexibility arises from the manufacturer's ability to control the porosity of the gel by varying the concentration of the acrylamide monomer and the proportion of the bis-acrylamide crosslinking agent relative to the monomer. PAGE is particularly useful for protein separations conducted in the presence of sodium dodecyl sulfate (SDS), either incorporated into the gel or included in the running buffer. Commonly used buffers are tris(hydroxymethyl)-aminomethane ("Tris") and bis(2-hydroxyethyl)amino-tris(hydroxymethyl)methane ("Bis-Tris"). Prominent among polyacrylamide gels for protein separations is one originally described by Laemmli, U.K., *Nature* 227: 680 (1970), and which contains Tris-HCl as a buffer at pH 8.8. Unfortunately, gels with pH values this high tend to hydrolyze over time, even when the gels are refrigerated. Hydrolysis reduces the migration distance of individual proteins within the gels and lowers the resolution of the protein bands. If the pH is lowered in an attempt to avert hydrolysis, a certain degree of sharpness in the resolution of separated proteins in the gel is lost, and the ability to obtain useful analyses of protein mixtures is often lost as well.

One means of overcoming this problem is the inclusion of triethanolamine in the gel, as disclosed in commonly owned co-pending U.S. patent application Ser. No. 12/552,104, filed Sep. 1, 2009. The present invention provides another means.

SUMMARY OF THE INVENTION

It has now been discovered that polyacrylamide gels that are resistant to hydrolysis, even during long-term storage, and yet are able to separate and resolve proteins under electrophoretic conditions into well-defined bands, are those that contain an ampholyte that is either taurine, asparagine, or a mixture of taurine and asparagine. It has also been discovered that pre-mixed gel-forming solutions containing taurine, asparagine, or both can be stored for extended periods and then cast into gels by the addition of a polymerization catalyst, and that protein separations can be performed on the resulting gels without a significant loss of protein resolution despite to the extended storage of the solutions. The pre-mixed solutions will contain the monomer and crosslinker, and optionally the buffer(s) and other components used in forming the final gel, but the solutions will not contain any polymerization catalysts. Both the stored gels and the stored pre-mixed gel-forming solutions will also contain buffers that are commonly used in electrophoresis gels; prominent examples of these buffers are Tris and Bis-Tris. In certain gels and pre-mixed solutions of the invention, a conventional ampholyte, examples of which are glycine and tricine (N-tris (hydroxymethyl)methylglycine), is also included, with the taurine or asparagine serving as conjugate ampholytes. Additional components such as stabilizers, pH modifiers, band-sharpening agents, and further buffers are also optionally included in certain embodiments.

When pre-cast and stored prior to use, the gels of the present invention offer the advantages of a long shelf life, i.e., resistance to hydrolysis during storage. Gels of this invention also offer the advantage of sharp protein resolution bands, in comparison to gels of other compositions, regardless of whether the gels have been stored prior to use, prepared from solutions that were stored prior to use, or used the same day as they were formulated and cast. A still further advantage is the ability of the gels to achieve sharp protein resolution at pH values approaching neutrality. Yet another advantage is the ability of the gels to achieve sharp protein resolution at high voltages and to perform the separations in correspondingly shorter run times. Gels in accordance with this invention are particularly useful with uniform (non-gradient) gels of high concentration and with gradient gels with high concentration maxima.

By stating that the gels of the present invention are resistant to hydrolysis during long-term storage or that the pre-mixed gel-forming solutions can, after long-term storage, be cast into gels that are resistant to hydrolysis, the inventors herein state, and demonstrate below, that the resulting gels remain capable of producing analytically useful electrophoretic separations of proteins despite the storage. The periods of storage over which the benefits of this invention are useful are periods in excess of one day, preferably three days or more, more preferably seven days or more, still more preferably one month or more, and still more preferably six months or more, and as much as a year. The storage conditions are those that are commonly used for pre-cast electrophoresis gels. Such conditions typically often include refrigeration at temperatures of less than 10° C., or within the range of about 1° C. to about 10° C., and most often a temperature of approximately 4° C. This invention is applicable to gels of any size or shape, including both tube gels and slab gels, as well as combinations of stacking and resolution gels.

These and other features, objects, and advantages of the invention are explained in more detail below.

DETAILED DESCRIPTION OF THE INVENTION AND PREFERRED EMBODIMENTS

Polyacrylamide gels in accordance with this invention are formed by the polymerization of acrylamide monomer and an acrylamide crosslinker in the presence of a polymerization catalyst according to methods well known in the art. The term "acrylamide crosslinker" denotes a molecule that reacts with acrylamide monomer to produce crosslinking during polymerization of the acrylamide monomer. Acylamide crosslinkers known in the art can be used; a prominent and widely used acrylamide crosslinker is N,N'-methylene-bis-acrylamide, also known as "bis-acrylamide" or simply "bis." Other acrylamide crosslinkers are ethylene-diacrylate (ED), diallyl-tartardiamide (DATD), and dihydroxyethylene-bisacrylamide (DHEBA).

The present invention is applicable to polyacrylamide gels of a wide range of porosities but, as noted above, is particularly useful with gels of high concentrations and accordingly low porosities, or with gels containing regions of high concentrations, such as gradient gels. According to common usage in the art, the total monomer (i.e., acrylamide plus crosslinker) concentration is expressed in weight percent and referred to by the symbol T, while the proportion of crosslinker to total monomer is likewise expressed in weight percent and referred to by the symbol C. The values of T and C are critical to the present invention, although in most applications, T will range from about 4% to about 25%, preferably from about 8% to about 15%, and C will range from about 2% to about 10%, preferably from about 2.5% to about 5%. In the high-concentration gels that are preferred in this invention, T ranges from about 12% to about 20%. For gels of uniform concentration, the T value is preferably from about 15% to about 18%, and for gradient gels, the maximum T value is preferably within the range of about 15% to about 25%, and most preferably about 20%. For gradient gels, the T value typically rises from a minimum of about 4% to a maximum of from about 12% to about 20%. Common examples of gradient gels are those with T values rising from 4% to 12%, or from 4% to 15%, or from 4% to 20%, with preferred C values as indicated above. Examples of catalysts known in the art to promote the polymerization of the monomers to form the gel are ammonium persulfate (APS), N,N'-tetramethylenediamine (TEMED), riboflavin, and β-dimethylaminopropionitrile, all used in catalytic amounts that are readily apparent to those skilled in the art. A typical catalyst concentration is 0.3 to 3.0 μg per mL of gel solution, and a common example is the combination of APS and TEMED, each at a concentration with this range. As noted above, in the case of pre-mixed solutions for long-term storage prior to being cast into gels, the catalyst(s) will be added at a point in time when the user is ready to cast the gel, often immediately before use of the gel or on the same day as the use.

The concentration of taurine or asparagine in the gel and in the pre-mixed solution can vary, but best results in most cases will be obtained with concentrations within the range of from about 100 mM to about 300 mM, and preferably about 150 mM to about 250 mM. Among taurine and asparagine, taurine is preferred. Glycine or tricine, when present, can vary in concentration as well, although best results in most cases will be obtained with glycine or tricine concentrations within the range of from about 50 mM to about 200 mM, and preferably about 100 mM to about 150 mM. The concentration ratio of taurine (or asparagine) to glycine (or tricine) is preferably greater than 1.0, and most preferably from about 1.25 to about 2.0. The concentration of Tris or Bis-Tris can likewise vary, and in most cases will produce best results at about 50 mM to about 200 mM. As in typical polyacrylamide gel preparations of the prior art, the pH of the monomer solution can be adjusted to the desired range with a suitable acid, examples of which are hydrochloric acid, sulfuric acid, acetic acid, boric acid, phosphoric acid, and glycolic acid. As needed, the pH can be adjusted to a value within the range of 6.4 to 9.0. A pH in the neutral range such as 6.4 to 7.0, for example, is preferred. As presently contemplated, the best modes of the invention are gradient gels containing 75 mM Tris-HCl, 200 mM taurine, 125 mM glycine, 23 mM HCl, and monomers at 4-12% T, 4-15% T, or 4-20% T, with C=2.6%.

In certain embodiments, the solution from which the gel is formed, and the pre-mixed solution in those embodiments of the invention relating to the use of pre-mixed solutions, further includes a weak acid or combination of two or more weak acids. Examples of weak acids are citric acid, maleic acid, phosphoric acid, acetic acid, and boric acid. Citric acid and maleic acid are preferred, with citric acid the most preferred. When present, the concentration of weak acid will preferably be within the range of about 0.01 mol/L (10 mM) to about 0.50 mol/L (500 mM), and most preferably from about 0.01 mol/L (10 mM) to about 0.05 mol/L (50 mM). A neutral salt can also be included to enhance the band resolution further, particularly over long-term storage. Examples of suitable salts are sodium chloride, sodium sulfate, sodium phosphate, potassium chloride, and potassium phosphate. When present, the concentration of the salt will preferably be within the range of about 0.01 mol/L (10 mM) to about 0.50 mol/L (500 mM), and most preferably from about 0.01 mol/L (10 mM) to about 0.05 mol/L (50 mM).

The gels of the present invention are used in the performance of electrophoretic separations in the same manner as conventional electrophoresis gels. A sample is loaded onto the cast gel, and a voltage differential is imposed across said gel to cause the proteins to migrate through said gel at migration rates that vary with the mass, charge, or both of the proteins and to separate into bands at different locations along the migration path within the gel according to their varying migration rates. As noted above, one advantage of the invention is that the gels can be run at high voltage, and accordingly shorter run times, without loss of resolution. A voltage differential of from about 35 to about 75 volts per cm of gel length, preferably from about 40 to about 50 volts per cm of gel length, can be used effectively.

EXAMPLE 1

This example illustrates the performance of polyacrylamide gels prepared with Tris-HCl and taurine within the scope of this invention, at varying levels of taurine, all stored at 4° C. for 72 hours between prior to use in electrophoretic separation.

A standard protein mixture containing myosin, beta-galactosidase, bovine serum albumin, ovalbumin, carbonic anhydrase, soybean trypsin inhibitor, lysosyme, and aprotinin was used. A sample buffer consisting of 62.5 mM Tris-HCl, 2% sodium dodecyl sulfate, 25% glycerol, and 0.01% bromophenol blue, at pH 6.8, and a running buffer consisting of 25 mM Tris, 192 mM glycine, and 0.1% sodium dodecyl sulfate, at pH 8.3, were used. Separations were performed at a constant voltage of 200V. All percents that are not otherwise indicated are by weight.

A series of polyacrylamide gels were cast in slab gel electrophoresis cassettes using 10% aqueous acrylamide/bis-acrylamide solution (T=10%) of which the bis-acrylamide constituted 2.6% of the monomer mixture (C=2.6%). Also included in the casting solutions were 150 mM Tris-HCl and taurine at concentrations of 20 mM, 40 mM, 80 mM, 150 mM, 160 mM, 200 mM, and 250 mM. The cassettes produced gels measuring 8 cm by 8 cm with a gel thickness of 1 mm. Once cast, the gels were stored at 4° C. over a weekend (i.e., approximately 72 hours). The standard protein mixture was then run in ten parallel lanes on each gel, the run performed on a MINI-PROTEAN III electrophoresis cell with a standard Tris-glycine SDS (sodium dodecyl sulfate) running buffer, at a constant voltage of 200V with run times ranging from 33 minutes to 50 minutes. The results were as follows:

- 20 mM taurine gel: normal protein distribution at 50 minutes, except for high molecular weight proteins which did not produce sharp bands
- 40 mM taurine gel: dye front distorted at 25 minutes, but by 48 minutes the dye front was straight and undistorted but the high molecular weight proteins did not produce sharp bands 80 mM taurine gel: dye fronts straight at 38 minutes, and the high molecular weight proteins produced bands that were more visible but still broad and unfocused 150 mM taurine gel: dye fronts wavy at 38 minutes, and the high molecular weight proteins produced bands that were more defined than in the 80 mM taurine gels but still not fully focused 160 mM taurine gel: dye fronts wavy at 38 minutes, results similar to those of 150 mM taurine gel 200 mM taurine gel: dye fronts and protein distribution normal at 33 minutes; high molecular weight protein bands sharper and more visible 250 mM taurine gel: protein distribution distorted at 38 minutes; high molecular weight proteins less sharp than at 200 mM These results indicate that while the gels all performed adequately, the 200 mM gel gave the clearest protein bands over the full range of molecular weight and the least distortion of the dye front.

EXAMPLE 2

This example is a shelf life study of polyacrylamide gels within the scope of the invention in an accelerated test. As in Example 1, the gels were cast in slab gel electrophoresis cassettes of the same dimensions using aqueous acrylamide/bis-acrylamide solution with T=10% and C=2.6%. Three gels contained 75 mM Tris-HCl and 200 mM taurine at pH 6.5; three additional gels contained 75 mM Tris-HCl, 83 mM asparagine, and 300 mM glycine at pH 6.5. One of each of the two types of gels was used immediately and the remaining gels were stored for different periods of time at 37° C. prior to use (one day at 37° C. is equivalent to one month at the typical storage temperature of 4° C.). The Tris-taurine gels were stored for 14 and 18 days, respectively, and the Tris-asparagine-glycine gels were stored for 8 and 15 days, respectively. The standard protein mixture was run on all gels in the manner described in Example 1.

In all cases, the gels produced acceptable protein distributions, indicating that the gels were stable during storage.

EXAMPLE 3

This example demonstrates the efficacy of the gels of the present invention at different running voltages, including voltages exceeding 200V. As in Examples 1 and 2, gels measuring 8 cm×8 cm×1 mm were cast in slab gel electrophoresis cassettes using aqueous acrylamide/bis-acrylamide solution with T=10% and C=2.6%, with 150 mM Tris-HCl and 200 mM taurine at pH 6.5. All gels were cast immediately upon combining the ingredients, and used immediately after casting. To each gel was applied two complex protein mixtures, one from soy isolate and the other from rat liver, together with four standards, each containing a mixture of manufactured proteins labeled with different dyes and spanning a range of electrophoretic mobility that encompasses the range of mobility of the proteins in each of the soy isolate and rat liver samples. The standards were obtained from Bio-Rad Laboratories, Inc. (Hercules, Calif., USA) bearing the general product name "Precision Plus Protein" standards. Identical gels loaded with identical samples were run in the MINI-PROTEAN III cell and in the TETRA Cell. Separations was performed at 200V (25 V/cm of gel length), 300V (37.5 V/cm of gel length), 350V (43.75 V/cm of gel length), and 400V (50 V/cm of gel length). Run times and final temperatures of the inner chamber (the upper buffer chamber) and outer chamber (the lower buffer chamber) for each run are listed in Table I below.

TABLE I

Variable Voltage Test Results

| Voltage | Run Time | Final Temperature | |
|---|---|---|---|
| | | Inner Chamber | Outer Chamber |
| 200 V | 32 min | 34° C. | 29° C. |
| 300 V | 22 min | 47° C. | 36° C. |
| 350 V | 16 min | 52° C. | 41° C. |
| 400 V | 9 min | 60° C. | 35.6° C. |

The images of the gels run at 400V showed that the faster-migrating bands were less sharp than the corresponding bands in the gels run at lower voltages, and a more visible bowing of the bands in the center lanes relative to the outer lanes. Nevertheless, the protein bands in each gel were clearly separated and identifiable and the distribution of the bands across the gel was essentially the same in all gels. These results indicate that the increased voltages allowed the separations to be performed in shorter run times without a significant loss in resolution and without leading to an increase in buffer temperature great enough to be detrimental to the gels or the separations.

EXAMPLE 4

This example demonstrates the efficacy of pre-mixed gel-forming solutions that were stored for extended periods of time before polymerization catalysts were added. The pre-mixed solutions were all aqueous acrylamide/bis-acrylamide solutions with T=10% and C=2.6%, and containing 150 mM Tris-HCl and 200 mM taurine at pH 6.5. Once prepared, they were stored for different periods of time in an accelerated aging test by using 37° C. as the storage temperature instead of the typical 4° C. After the solutions were stored for their designated time periods, 2.0 µL of TEMED and 0.5 mg of APS were added to milliliter of each solution, and the resulting solutions were cast into gels measuring 8 cm×8 cm×1 mm. The gels were then loaded with soy isolate and rat liver samples plus samples of three of the "Precision Protein Plus" standards, and run at 200V in the TETRA Cell.

Two identical gels were cast and run after zero days of storage of the pre-mixed solution, four other gels after six days of storage at 37° C. (equivalent to six months at 4° C.), and two other gels after thirteen days of storage at 37° C. (equivalent to thirteen months at 4° C.). The results in all cases were well-defined bands that were visually differentiable, although the bands on the gels cast after thirteen days of storage were lighter and less sharp than the bands on the gels cast after zero days of storage and after six days of storage.

COMPARATIVE EXAMPLE

This example compares the performance of a gel containing serine as the conjugate ampholyte with a gel containing taurine as the conjugate ampholyte. The former is outside the scope of the present invention while the latter is within the scope. The compositions of the gels used are shown in Table II below. The gels were otherwise identical to those of the preceding examples, and each was formulated, cast, and used, all within the same day (less than six hours).

TABLE II

Gel Compositions for Comparative Tests

| Gel of Invention | Gel Containing Serine |
|---|---|
| Acrylamide/Bis-Acrylamide: T = 10%, C = 2.6% | Acrylamide/Bis-Acrylamide: T = 10%, C = 2.6% |
| 75 mM Tris | 75 mM Tris |
| 200 mM Taurine | 200 mM Serine |
| 125 mM Glycine | 125 mM Glycine |
| 37 mM HCl | 37 mM HCl |
| pH: 6.5 | pH: 6.5 |

One of each gel was placed in the MINI-PROTEAN III cell and one of each was also placed in the TETRA Cell (also of Bio-Rad Laboratories, Inc.). The standard protein mixture was run on all gels in the manner described in Example 1. A comparison of the gels showed that mid-range bands in the serine-containing gel were less well defined than the corresponding bands in the taurine-containing gel.

In the claims appended hereto, the terms "a" and "an" are each intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A polyacrylamide gel comprising:
    a buffer selected from the group consisting of tris(hydroxymethyl)aminomethane and bis(2-hydroxyethyl) amino-tris(hydroxymethyl)methane, and
    taurine at a concentration of from about 100 mM to about 300 mM,
in a gel matrix consisting of crosslinked polyacrylamide, said polyacrylamide gel having a pH of from about 6.4 to about 7.0.

2. The polyacrylamide gel of claim 1 wherein said crosslinked polyacrylamide constitutes from about 4% to about 25% by weight of said gel.

3. The polyacrylamide gel of claim 1 wherein said polyacrylamide gel comprises polyacrylamide at about 4% to about 25% by weight of said gel and an acrylamide crosslinker at about 2% to about 10% by weight of said polyacrylamide.

4. The polyacrylamide gel of claim 1 wherein said polyacrylamide gel comprises polyacrylamide at about 8% to about 15% by weight of said gel and an acrylamide crosslinker at about 2.5% to about 5% by weight of said polyacrylamide, and said taurine is at a concentration of from about 150 mM to about 250 mM.

5. The polyacrylamide gel of claim 1 wherein said gel is a gradient gel with a gradient of polyacrylamide concentration extending from a minimum value of about 4% by weight to a maximum value that is within the range of about 12% to about 20% by weight.

6. The polyacrylamide gel of claim 1, further comprising a conjugate ampholyte selected from the group consisting of glycine and tricine, wherein the molar concentration ratio of taurine to the conjugate ampholyte is greater than 1.0.

7. The polyacrylamide gel of claim 6, wherein the molar concentration ratio of taurine to the conjugate ampholyte is from about 1.25 to about 2.0.

8. A pre-mixed solution for casting to form a polyacrylamide electrophoresis gel, said pre-mixed solution comprising the following ingredients dissolved in water:
    (i) acrylamide monomer,
    (ii) an acrylamide crosslinker,
    (iii) a buffer selected from the group consisting of tris (hydroxymethyl)aminomethane and bis(2-hydroxyethyl)amino-tris(hydroxymethyl)methane, and
    (iv) taurine,
wherein said taurine is at a concentration of from about 100 mM to about 300 mM in said pre-mixed solution, and said pre-mixed solution has a pH of from about 6.4 to about 7.0.

9. The pre-mixed solution of claim 8 wherein said acrylamide monomer and said acrylamide crosslinker together constitute from about 4% to about 25% by weight of said pre-mixed solution.

10. The pre-mixed solution of claim 8 wherein said acrylamide crosslinker constitutes from about 2% to about 10% by weight of the total of said acrylamide monomer and said acrylamide crosslinker.

11. The pre-mixed solution of claim 8 wherein said acrylamide monomer and said acrylamide crosslinker together constitute from about 4% to about 25% by weight of said pre-mixed solution, and said acrylamide crosslinker constitutes from about 2% to about 10% by weight of the total of said acrylamide monomer and said acrylamide crosslinker.

12. The pre-mixed solution of claim 8 wherein said acrylamide monomer and said acrylamide crosslinker together constitute from about 8% to about 15% by weight of said pre-mixed solution, said acrylamide crosslinker constitutes from about 2.5% to about 5% by weight of the total of said acrylamide monomer and said acrylamide crosslinker, and said taurine is at a concentration of from about 150 mM to about 250 mM.

13. The pre-mixed solution of claim 8 wherein said acrylamide crosslinker is bis-acrylamide.

14. The pre-mixed solution of claim 8, further comprising a conjugate ampholyte selected from the group consisting of glycine and tricine, wherein the molar concentration ratio of taurine to the conjugate ampholyte is greater than 1.0.

15. The pre-mixed solution of claim 14, wherein the molar concentration ratio of taurine to the conjugate ampholyte is from about 1.25 to about 2.0.

16. A method for forming a polyacrylamide electrophoresis gel, said method comprising:
    (a) storing the pre-mixed solution of claim 8
        for a period of time exceeding 24 hours;
    (b) adding to said pre-mixed solution a polymerization catalyst to cause said acrylamide and acrylamide crosslinker to polymerize to form a crosslinked polyacrylamide and to thereby transform said pre-mixed solution to a gel.

17. The method of claim 16 wherein said period of time exceeds seven days.

18. The method of claim 16 wherein said period of time is between seven days and one year.

19. The method of claim 16 wherein said period of time is between one month and one year.

20. The method of claim 16 wherein said period of time is between six months and one year.

21. The method of claim 16 wherein step (a) is performed at a temperature of from about 1° C. to about 10° C.

22. The method of claim 16 wherein said acrylamide monomer and said acrylamide crosslinker together constitute from about 4% to about 25% by weight of said pre-mixed solution.

23. The method of claim 16 wherein said acrylamide crosslinker constitutes from about 2% to about 10% by weight of the total of said acrylamide monomer and said acrylamide crosslinker.

24. The method of claim 16 wherein said acrylamide monomer and said acrylamide crosslinker together constitute from about 4% to about 25% by weight of said pre-mixed solution, and said acrylamide crosslinker constitutes from about 2% to about 10% by weight of the total of said acrylamide monomer and said acrylamide crosslinker.

25. The method of claim 16 wherein said acrylamide monomer and said acrylamide crosslinker together constitute from about 8% to about 15% by weight of said pre-mixed solution, said acrylamide crosslinker constitutes from about 2.5% to about 5% by weight of the total of said acrylamide monomer and said acrylamide crosslinker, and said taurine is at a concentration of from about 150 mM to about 250 mM.

26. A method for separating proteins in a liquid sample by electrophoresis, said method comprising:
(a) loading said sample onto the polyacrylamide gel of claim 1; and
(b) imposing a voltage differential across said gel to cause said proteins to migrate through said gel at migration rates that vary with the mass, charge, or both of said proteins and to separate into bands within said gel due to said varying migration rates.

27. The method of claim 26 wherein said polyacrylamide constitutes from about 4% to about 25% by weight of said gel.

28. The method of claim 26 wherein said polyacrylamide constitutes from about 4% to about 25% by weight of said gel, and an acrylamide crosslinker constitutes from about 2% to about 10% by weight of said polyacrylamide.

29. The method of claim 26 wherein said polyacrylamide constitutes from about 8% to about 15% by weight of said gel, an acrylamide crosslinker constitutes from about 2.5% to about 5% by weight of said polyacrylamide, and said taurine is at a concentration of from about 150 mM to about 250 mM.

30. The method of claim 26 wherein said gel is a gradient gel with a gradient of polyacrylamide concentration extending from a minimum value of about 4% by weight to a maximum value that is within the range of about 12% to about 20% by weight.

31. The method of claim 26 wherein said voltage differential is from about 35 to about 75 volts per cm of gel length.

32. The method of claim 26 wherein said voltage differential is from about 40 to about 50 volts per cm of gel length.

* * * * *